(12) United States Patent
Petito et al.

(10) Patent No.: US 8,168,599 B2
(45) Date of Patent: *May 1, 2012

(54) COMPOSITION AND METHOD FOR HEALING TISSUES

(76) Inventors: George D. Petito, Bethlehem, PA (US); Anita M. Petito, Bethlehem, PA (US)

( * ) Notice: Subject to any disclaimer, the term of this patent is extended or adjusted under 35 U.S.C. 154(b) by 152 days.

This patent is subject to a terminal disclaimer.

(21) Appl. No.: 12/659,656

(22) Filed: Mar. 16, 2010

(65) Prior Publication Data

US 2010/0173868 A1    Jul. 8, 2010

Related U.S. Application Data

(63) Continuation of application No. 11/071,464, filed on Mar. 4, 2005, now Pat. No. 7,691,829, which is a continuation-in-part of application No. 10/457,599, filed on Jun. 10, 2003, now abandoned, which is a continuation of application No. 09/983,274, filed on Oct. 23, 2001, now abandoned, which is a continuation-in-part of application No. 09/360,169, filed on Jul. 26, 1999, now Pat. No. 6,476,005, which is a continuation-in-part of application No. 09/046,710, filed on Mar. 24, 1998, now abandoned.

(51) Int. Cl.
*A61K 31/70* (2006.01)
*A61K 31/715* (2006.01)
*A61K 31/727* (2006.01)
*A61K 47/00* (2006.01)

(52) U.S. Cl. ............... 514/42; 514/53; 514/54; 514/56; 514/57; 514/801

(58) Field of Classification Search .................... 514/42, 514/53, 54, 56, 57, 801
See application file for complete search history.

(56) References Cited

U.S. PATENT DOCUMENTS

| | | | |
|---|---|---|---|
| 1,950,100 A | 3/1934 | Chandall, Jr. et al. | |
| 4,006,224 A | 2/1977 | Prudden | |
| 4,216,204 A | 8/1980 | Robertson | |
| 4,265,233 A | 5/1981 | Sugitachi et al. | |
| 4,294,241 A | 10/1981 | Miyata | |
| 4,344,967 A | 8/1982 | Easton et al. | |
| 4,347,234 A | 8/1982 | Wahlig et al. | |
| 4,402,979 A | 9/1983 | Shen et al. ............... | 514/569 |
| 4,407,787 A | 10/1983 | Stemberger | |
| 4,416,873 A | 11/1983 | Puchalski et al. | |
| 4,455,302 A | 6/1984 | Robertson | |
| 4,640,912 A | 2/1987 | Hausman | |
| 4,745,098 A | 5/1988 | Michaeli ............... | 514/2 |
| 4,759,354 A | 7/1988 | Quarfoot | |
| 4,804,745 A | 2/1989 | Koepff et al. | |
| 4,808,570 A | 2/1989 | Michaeli | |
| 4,813,942 A | 3/1989 | Alvarez | |
| 4,837,024 A | 6/1989 | Michaeli | |
| 4,841,962 A | 6/1989 | Berg et al. | |
| 4,863,907 A | 9/1989 | Sakurai et al. | |
| 4,892,736 A | 1/1990 | Goodson | |
| 4,906,460 A | 3/1990 | Kim et al. | |
| 4,921,691 A | 5/1990 | Stockel | |
| 4,950,699 A | 8/1990 | Holman | |
| 4,983,580 A | 1/1991 | Gibson | |
| 5,064,653 A | 11/1991 | Sessions et al. | |
| 5,081,106 A | 1/1992 | Bentley et al. | |
| 5,114,718 A | 5/1992 | Damani | |
| 5,116,620 A | 5/1992 | Chvapil et al. | |
| 5,141,928 A | 8/1992 | Goldman | |
| 5,171,574 A | 12/1992 | Kuberasampath | |
| 5,188,826 A | 2/1993 | Chandrasekaran et al. ............... | 424/78.04 |
| 5,196,185 A | 3/1993 | Silver et al. | |
| 5,252,339 A | 10/1993 | Cristofori et al. | |
| 5,300,306 A | 4/1994 | Alvarado et al. | |
| 5,332,579 A | 7/1994 | Umbdenstock | |
| 5,364,845 A | 11/1994 | Henderson | |
| 5,366,964 A | 11/1994 | Lindstrom et al. | |
| 5,399,351 A | 3/1995 | Leshchiner et al. | |
| 5,438,043 A | 8/1995 | Ljungqvist | |
| 5,442,053 A | 8/1995 | Valle et al. | |
| 5,498,606 A | 3/1996 | Soll et al. | |
| 5,512,291 A | 4/1996 | Li | |

(Continued)

FOREIGN PATENT DOCUMENTS

EP    0 450 671 A1    10/1991

(Continued)

OTHER PUBLICATIONS

English Machine Translation of JP 07-223966 A, Date—Aug. 1995, Country—Japan, Name—Iwadare, Yasuhiko.*

*Primary Examiner* — Shaojia Anna Jiang
*Assistant Examiner* — Everett White
(74) *Attorney, Agent, or Firm* — Richard C. Litman

(57) ABSTRACT

The composition and method for healing tissues is a medicinal composition for facilitating the growth, protection and healing of tissues and cells in animals and humans. The composition is formulated as a either a powder, gel, paste, film, fluid injectable, rehydratable freeze-dried paste or sponge, sprayable solution, topically applied patch with adhesive and reservoir system, an intermediate for coatables such as films and bandages, a matrix for membranes, or as a matrix of flexible polymer(s), or delivered as either an orally ingestible liquid, tablet or capsule. The main ingredient of the formulated compositions is hydrolyzed collagen, which can be combined with polysulfated glycosaminoglycans, hyaluronic acid or salts thereof, or a glucosamine salt, and mixtures thereof. The composition may be formulated as an aqueous eye drop solution.

7 Claims, No Drawings

U.S. PATENT DOCUMENTS

| | | |
|---|---|---|
| 5,531,791 A | 7/1996 | Wolfinbarger, Jr. |
| 5,589,451 A | 12/1996 | Wilson .............................. 512/2 |
| 5,631,243 A | 5/1997 | Kelman et al. |
| 5,639,796 A | 6/1997 | Lee |
| 5,654,009 A | 8/1997 | Hata et al. |
| 5,676,967 A | 10/1997 | Williams et al. |
| 5,720,955 A | 2/1998 | Weiner et al. |
| 5,759,570 A | 6/1998 | Arnold |
| 5,837,278 A | 11/1998 | Geistlich et al. |
| 5,840,715 A | 11/1998 | Florio |
| 5,871,767 A | 2/1999 | Dionne et al. |
| 5,929,050 A | 7/1999 | Petito |
| 5,948,766 A | 9/1999 | Milan et al. |
| 6,019,971 A | 2/2000 | Weiner et al. |
| 6,022,557 A | 2/2000 | Maser |
| 6,136,341 A | 10/2000 | Petito |
| 6,162,787 A | 12/2000 | Sorgente et al. |
| 6,476,005 B1 | 11/2002 | Petito et al. |
| 7,691,829 B2 * | 4/2010 | Petito et al. .................... 514/54 |

FOREIGN PATENT DOCUMENTS

| | | |
|---|---|---|
| EP | 590655 A1 * | 4/1994 |
| GB | 896940 | 5/1962 |
| JP | 07223966 A * | 8/1995 |

* cited by examiner

COMPOSITION AND METHOD FOR HEALING TISSUES

CROSS-REFERENCE TO RELATED APPLICATIONS

This is a continuation of my prior application Ser. No. 11/071,464, filed Mar. 4, 2005 now U.S. Pat. No. 7,691,829, which is a continuation-in-part of my prior application Ser. No. 10/457,599, filed Jun. 10, 2003 now abandoned, which is a continuation of application Ser. No. 09/983,274 filed Oct. 23, 2001 now abandoned, which is a continuation-in-part of application Ser. No. 09/360,169 filed Jul. 26, 1999, now U.S. Pat. No. 6,476,005, which is a continuation-in-part of application Ser. No. 09/046,710 filed Mar. 24, 1998, now abandoned.

BACKGROUND OF THE INVENTION

1. Field of the Invention

The present invention relates to a method and composition for growing, protecting, and healing tissues and cells of animals or humans. The invention particularly pertains to a method for repairing connective and other tissues, and, in particular, wound healing and scar reduction by administering a composition comprising a hydrolyzed collagen as the basic ingredient, preferably in combination with at least one therapeutic agent selected from the group consisting of a polysulfated glycosaminoglycan, hyaluronic acid and salts thereof, and a glucosamine salt.

2. Description of the Related Art

Just as nature has provided the skin as a barrier for protection, it has also provided mechanisms for skin repair. Depending upon the nature of the injury, this repair process may take hours, days, months, or even years. Many factors determine the length of times it takes for an injured skin to heal. Pathogenic contaminants may enter the body through the wound until the skin's integrity is restored. For this reason, it desirable to heal open wounds as quickly as possible.

Open wounds in the skin are a potential gateway for infectious or contaminating material to enter the body. The skin is a protective barrier to external contaminants. When the skin is damaged with an open breach, these contaminants are free to enter the body. Once inside the body, these contaminants may have effects of varying degrees, but almost always become more difficult to treat, and consequently slow the healing process of the original wound.

To fight infection, wound management traditionally involves an initial cleansing of the affected area to remove any contaminants such as dirt, clothing particles, or other debris. Damaged tissues and foreign materials are removed when necessary, and antiseptic agents are applied to sterilize the injured area. Sterile dressings are often applied, and periodically changed, to keep the injured area as clean and sterile as possible. Complex biological mechanisms occur during the healing process such as chemical signals attracting fibroblast cells to the wound site which ultimately generate connective structures mainly of collagen. Endothelial cells generate new blood capillaries that nurture the new growth. The cell growth continues until the open wound is filled by forming permanent new tissue.

Because shortened periods of healing result in shortened exposure time, it would be beneficial to have any open wound heal as quickly as possible.

The related art of interest describes various tissue repairing compositions, but none discloses the present invention. There is an urgent need for a composition useful for wound healing, scar reduction and repairing of damaged tissue, e.g., connective tissue.

Applicant has obtained the following patents related to this invention. U.S. Pat. No. 5,929,050 issued on Jul. 27, 1999, titled "Chondroitin Sulfate Composition And Method For Wound Treatment" describes a composition and method for treating open wounds comprising the application or injection of a sterilized aqueous solution of 90 to 110 mg/mL chondroitin sulfate which can contain hydrolyzed collagen, sodium hyaluronate, and glucosamine sulfate or chloride.

U.S. Pat. No. 6,136,341 issued on Oct. 24, 2000, titled "Collagen Containing Tissue Adhesive" describes a method for applying a wound dressing composition comprising a hydrolyzed Type I collagen having an average molecular weight of 1,000 to 10,000 gm. with uncleaved peptide ends in a physical form of either a powder, gel, paste, and film. The composition can include a cross-linking agent selected from the group consisting of a humectant, propylene glycol, sorbitol, and glycerine. A preservative such as benzyl alcohol or paraben can be added. The wound dressing method consisting essentially of the steps of: (a) debriding and cleansing an open wound site with a saline solution; (b) drying surrounding skin; (c) applying the claimed composition; (d) applying a nonsticking dressing; and (e) repeating steps (b) to (d) every 24 hours.

The use of medical hydrolysates and collagen in wound healing has been the subject of previous patents. U.S. Pat. No. 5,498,606 issued to David B. Soll et al. on Mar. 12, 1996, describes the protection against exfoliation of the cells of the coverings and linings of internal human and animal tissues by the topical application or injection of 40 to 55 wt. % of the three isomers A, B and C of chondroitin sulfate prior to or during the trauma, using as (1) a surgical irrigating solution, (2) interarticular injection into joints for protecting the joint cells, (3) reducing aseptic inflammation, and (4) can be used for preserving human and animal cells and tissues for later in vivo use and stored by adding 1 to 20 wt. % of the storage solution. Chondroitin sulfate A is derived from whale cartilage; chondroitin sulfate B is derived from porcine skin; and chondroitin sulfate C is derived from shark cartilage.

U.S. Pat. Nos. 4,216,204 and 4,455,302 issued to Harry J. Robertson on Aug. 5, 1980, and Jun. 19, 1984, respectively, describes a medical protein hydrolysate and processes for making and using the protein hydrolysate. The protein hydrolysate is made in powder or gel form from ground poultry feet for application to traumatized areas. The composition is distinguishable for being obtained from young poultry feet.

Other patents describe the use of collagen in various wound dressings. U.S. Pat. No. 4,759,354 issued to Alan J. Quarfoot on Jul. 26, 1988, describes a wound dressing including a vapor-permeable layer and an absorbent adhesive layer containing collagen. U.S. Pat. No. 4,837,024 issued to Dov Michaeli on Jun. 6, 1989, describes compositions, articles and methods for improving wound healing. The wound is contacted by a combined suspension of collagen and a mixture of chemotactic glycosaminoglycans (heparin, heparin sulfate and alginate) for improved healing. U.S. Pat. No. 4,950,699 issued to Daniel G. Holman on Aug. 21, 1990, describes a wound dressing incorporating 0.1% to 10% collagen by weight in a water-based acrylic adhesive layer. U.S. Pat. No. 5,081,106 issued to J. Peter Bentley et al. on Jan. 14, 1992, describes a wound dressing protocol utilizing collagen (atelopeptide) gelatin formed with iodine. U.S. Pat. No. 5,116,620 issued to Milos Chvapil et al. on May 26, 1992, describes an antimicrobial wound dressing, having a layer of collagen impregnated with lyophilized, stabilized chlorine-containing compounds, e.g., sodium chlorate and sodium chlorite, to generate chlorine dioxide, and citric acid. U.S. Pat. No. 5,759,570 issued to Peter S. Arnold on Jun. 2, 1998, describes a multi-layer wound dressing comprising a wound contact layer (collagen material), an absorbent layer and an outer protective membrane. U.S. Pat. No. 6,022,557 issued to Franz Maser on Feb. 8, 2000, describes a wound covering material based on partially modified collagen fibers with amidated nitrogen, glucosamine and galactosamine. U.S. Pat. No. 4,407,787 issued to Axel Stemberger on Oct. 4, 1983, describes a dressing containing collagen in combination with a resorbable biopolymer (fibrinogen or gelatin). U.S. Pat. No. 4,265,233 issued to Akio Sugitachi et al. on May 5, 1981, describes a wound healing material containing collagen with a blood coagulation Factor XIII fixed thereto which promotes formation of stabilized fibrin at the wound site. U.S. Pat. No. 4,294,241 issued to Teruo Miyata on Oct. 13, 1981, describes a method for preparing collagen skin dressing in gel or sheet form from enzyme-solubilized and/or chemically modified collagen. U.S. Pat. No. 5,196,185 issued to Fred Silver et al. on Mar. 23, 1993, describes a collagen-based wound dressing and a method of application. The dressing uses 1 to 50 micron size type I and/or type III collagen in an aerosol delivery system. U.S. Pat. No. 4,347,234 issued on Aug. 31, 1982, to Helmut Wahlig et al. describes a collagen containing shaped mass composition comprising collagen and a polymer selected from hydroxyalkanoic acids, amino acids, hydrolyzed collagen, and hydrolyzed elastin. U.S. Pat. No. 4,344,967 issued on Aug. 17, 1982, to Ian A. Easton et al. describes a film forming composition comprising a partially hydrolyzed collagen protein having a molecular weight from 3,000 to 45,000, glycerol and ethanol to form a protective barrier on a cow's teats. U.S. Pat. No. 4,416,873 issued on Nov. 22, 1983, to Eugene Puchalski et al. describes an allantoin-hydrolyzed collagen containing cologne, after-shave lotion or skin toner. U.S. Pat. No. 4,804,745 issued on Feb. 14, 1989, to Peter Koepff et al. describes hydrolyzed collagens added to agents for the treatment of arthroses. U.S. Pat. No. 4,906,460 issued on Mar. 6, 1990, to Wendy W. Kim et al. describes the addition of hydrolyzed collagen and silk amino acids to hair treatment compositions. U.S. Pat. No. 5,114,718 issued on May 19, 1992, to Nalinkant C. Damani describes sustained release compositions for treating periodontal disease comprising collagen, an antimicrobial, and vitamins.

Type I collagen is found in numerous medical applications in the patent literature. U.S. Pat. Nos. 6,019,971 issued on Feb. 1, 2000, and 5,720,955 issued on Feb. 24, 1988, to Howard L. Weiner et al. describe the treatment of autoimmune arthritis by orally administering Type I, II and III whole collagen protein or collagen peptide fragments. U.S. Pat. No. 5,171,574 issued to Thangavel Kuberasampath et al. on Dec. 15, 1992, describes Type I bone collagen particles used in a matrix for implants. The collagen is treated with collagen fibril modifying substance such as acidified acetonitrile, chloroform or dichloromethane. U.S. Pat. No. 5,676,967 issued to Jeffrey M. Williams et al. on Oct. 14, 1997, describes a mesh matrix wound dressing comprising a mixture of Types I and III collagen with and oligosaccharide. U.S. Pat. No. 5,512,291 issued to Shu-Tung Li on Apr. 30, 1996, describes a method of making vascular wound dressings from Type I collagen to repair blood vessels. U.S. Pat. No. 4,841,962 issued to Richard A. Berg et al. on Jun. 27, 1989, describes a wound dressing which promotes progressive healing and comprises a crosslinked Type I or II collagen matrix, a bioabsorbable adhesive coated on one surface thereof, a multi-layer polymer film secured to an opposite surface thereof, and an adhesive layer. U.S. Pat. No. 5,531,791 issued on Jul. 2, 1996, to Lloyd Wolfinbarger, Jr. describes a biocompatible collagen/demineralized human bone composite material formulated as a fluid injectable, gel or rehydratable freeze dried paste. U.S. Pat. No. 5,631,243 issued on May 20, 1997, to Charles D. Kelman et al. describes a collagen-based viscoelastic solution containing mucopolysaccharides for ocular visco-surgery. U.S. Pat. No. 5,639,796 issued on Jun. 17, 1997, to Clarence C. Lee describes an injectable composition for replacing body lubricating fluids comprising polymer particles having a diameter between 4 to 150 microns selected from a group including chondroitin sulfate, hyaluronic acid, alginate, collagen, and cross-linked elastin and hyaluronic acid. U.S. Pat. No. 5,654,009 issued on Aug. 5, 1997, to Takehisa Hata et al. describes a delayed action composition comprising a core of a drug and a swelling agent, and an outer membrane comprising sodium hyaluronate or collagen for dispensing by oral, intramuscular or subcutaneous means. U.S. Pat. No. 5,948,766 issued on Sep. 7, 1999, to Adam Milan et al. describes a hydrolyzed collagen (Type I and III) composition combined with calcitonin, calcium salts and/or progesterone for treating osteoporosis. The hydrolyzed collagen obtained from gelatin or animal collagenic connective tissue has an average molecular weight from 1 to 40 kDaltons. The composition can be formulated in the form of paste, syrup, solution granules, pills or powder. The composition is distinguishable for being cross-linked.

U.S. Pat. No. 6,162,787 issued on Dec. 19, 2000, describes a composition for treating arthritis comprising insoluble native collagen Type II, glucosamine sulfate, chondroitin sulfate, ascorbate, boron, and magnesium. The medications can be administered orally in the form of a tablet, capsule, powder, suspension or an aerosol spray. The collagen is obtained from the breastbone of healthy chickens. The composition is distinguishable for treating arthritis and containing boron and magnesium.

Other compositions and methods for aiding wound healing have also been the subjects of previous patents, but are less related to the present invention. Examples of previous patents describing wound healing are diverse: U.S. Pat. No. 4,813,942, issued to Oscar M. Alvarez on Mar. 21, 1989, describes a three-step wound treatment method and dressing, wherein the third phase dressing contains 0.05% to 20% hyaluronic acid; U.S. Pat. No. 4,921,691 issued to Richard F. Stockel on May 1, 1990, describes spray-on wound dressing compositions containing anti-bacterial organosilicon quaternary ammonium salt chemically bonded to a polymer such as collagen; U.S. Pat. No. 5,300,306 issued to Carlos A. Alvarado et al. on Apr. 5, 1994, describes a tissue-equivalent membrane for treating burns from bovine esophageal tissue; European patent document 0 530 982 A1 published on Mar. 10, 1993, for James V. Cartmell et al. describes a wound dressing for deep wounds containing polyhydric alcohol, isophoronediisocyanate terminated prepolymer, polyethylene oxide based diamine, sodium chloride, and water; U.S. Pat. No. 4,892,736 issued on Jan. 9, 1990, to J. Max Goodson describes an intra-pocket delivery device for treatment of periodontal diseases comprising tetracycline mixed with ethylene vinyl acetate copolymer; and European patent document 0 450 671 A1 published Oct. 9, 1991, for Wilhelmus E. Hennick et al. describes a wound dressing and method of preparing the same comprising a lower layer of an antibacterial agent added hydrogel of a cross-linked polymer added to other elastomer layers. U.S. Pat. No. 5,064,653 issued on Nov. 12, 1991, to Robert W. Sessions et al. describes an absorbent hydrophilic foam composition for wound dressings comprising an in situ reaction product of an isocyanatecapped polyether prepolymer, a hydrophilic agent, alcohol, a wetting agent, and water. U.S. Pat. No. 5,332,579 issued on Jul. 26, 1994, to Anthony J. Umbdenstock describes nutritional supplement compositions for optimizing cellular health for smoking and alcohol addicted patients comprising amino acids, minerals, vitamins, and herbs.

Chondroitin sulfate and other GAGs used to aid healing or skin trauma have been the subject of the following patents. U.S. Pat. No. 4,808,570 issued on Feb. 28, 1989, to Dov Michaeli describes compositions and method for improving wound healing, wherein the composition contains a suspension of 7-10 mg./ml. collagen and 250-350 microgm./ml. glycosaminoglycans such heparin, heparin sulfate, and alginate which is not covalently crosslinked. The compositions are distinguishable for teaching against the use of chondroitin sulfate.

U.S. Pat. No. 4,640,912 issued on Feb. 3, 1987, to Marvin S. Hausman describes the use of "active" chondroitin sulfate A and "active" chondroitin sulfate C to prevent cancer cell implantation, bacterial infestation, trauma, irritation or damage from foreign instruments in the kidney, renal pelvis, ureter, bladder, urethra, etc. by irrigation with a solution containing the chondroitin sulfate.

U.S. Pat. No. 4,863,907 issued on Sep. 5, 1989, to Katukiyo Sakurai et al. describes cross-linked glycosaminoglycans (GAGs) and their salts, but excluding hyaluronic acid. The GAG can be chondroitin sulfate, heparin, heparin sulfate, keratin sulfate or keratinpolysulfate, which is reacted with either epichlorohydrin or epibromohydrin. Cross-linked GAGs with a cross-linking index of 0.05 or more per mole are used for various medical and cosmetic reasons. Cross-linked GAGs are not used in the present invention.

U.S. Pat. No. 5,366,964 issued on Nov. 22, 1994, to Richard L. Lindstrom et al. describes a viscoelastic solution containing 0.01-10% chondroitin sulfate, 0.01-10% hydroxypropyl-methylcellulose, and 0.01-10% sodium hyaluronate among other ingredients for use in ocular and surgical applications.

U.S. Pat. No. 4,983,580 issued on Jan. 8, 1991, to David R. Gibson describes methods and materials for use in corneal wound healing. A preferred embodiment includes fibronectin and chondroitin sulfate in a corneal mortar composition. Fibronectin is not used in the present invention.

U.S. Pat. No. 5,399,351 issued on Mar. 21, 1995, to Edward Leshchiner et al. describes the preparation and use of biocompatible viscoelastic gel slurries comprising a first phase of GAGs cross-linked with a polysaccharide and a protein, and a second phase comprising a polymer solution of either polysaccharides, polyvinylpyrrolidone and polyethylene oxide. A gel containing cross-linked GAGs controls adhesion formation between tissues resulting from surgical intervention. Cross-linked GAGs are not used in the present invention.

U.S. Pat. No. 5,837,278 issued on Nov. 17, 1998, to Peter Geistlich et al. describes a resorbable collagen membrane for wound healing comprising at least 90 wt. % collagen which is cross-linked with formaldehyde, etc. and impregnate the fibrous side of the membrane with a glycosaminoglycan (GAG) such as hyaluronic acid, chondroitin sulfate, dermatin sulfate or keratin sulfate. Cross-linked GAGS are not used in the present invention.

U.S. Pat. No. 5,871,767 issued on Feb. 16, 1999, to Keith E. Dionne et al. describes methods for treatment of neurodegenerative conditions by implanting a vehicle with a biocompatible jacket in the form of a hollow fiber or a flat sheet and a matrix core, wherein the matrix contains cross-linked collagen and glycosaminoglycans (hyaluronic acid, chondroitin sulfate, heparin, and heparin sulfate). Cross-linked GAGS are not used in the present invention.

The following art describes various oral nutritional products for improving various physiological functions of the human body, and discussed according the perceived relevance to the present invention.

U.S. Pat. No. 5,141,928 issued on Aug. 25, 1992, to Lawrence Goldman describes ophthalmic medications containing glycosaminoglycan polysulfates (GAGPS) or mucopolysaccharides having a molecular weight in the range of 5,000 to 20,000 Daltons combined with antibiotics for treating eye infections and antimicrobial agents such as pilocarpine or epinephrine for glaucoma. GAGPS include chondroitin sulfate and hyaluronic acid that contain hexosamines. The medicament composition is distinguishable for its reliance on GAGPS, antibiotics, and anti-microbial agents which is limited to human eye use.

U.S. Pat. No. 1,950,100 issued on Mar. 6, 1934, to Lathan A. Crandall, Jr. et al. describes a chemical composition for the treatment of migraine, urticarial eruptions, peptic ulcers, and multiple sclerosis, inter alia. Chondroitin sulfate is combined with either calcium, magnesium or iron. The composition is distinguishable for its sole ingredient containing a sulfate which is useful only for other human ailments than tissue and cell growth.

U.S. Pat. No. 5,364,845 issued on Nov. 15, 1994, to Robert W. Henderson describes a therapeutic composition administered in capsules for the protection, treatment and repair of connective tissue in mammals. The medicament contains 250-3000 mg. glucosamine hydrochloride or sulfate, 50-1000 mg. chondroitin sulfate and 150-950 mg. manganese ascorbate. The dosages for human use are in the lower regions of the given ranges. The composition is distinguishable from the present invention for not requiring hydrolyzed or native collagen, sodium hyaluronate, and L-malic acid.

U.S. Pat. No. 5,438,043 issued on Aug. 1, 1995, to Olle Ljungqvist describes a hypotonic solution for ingestion by patients undergoing surgery for suppressing insulin resistance. The solution contains dextrin, maltose, glucose, sodium chloride, and sodium hydroxide at a pH between 5.6 to 6.8. The composition is distinguishable for its absence of every ingredient in the present invention.

U.S. Pat. No. 5,442,053 issued on Aug. 15, 1995, to Francesco della Valle et al. describes a pharmaceutical composition and method for treating ophthalmic conditions, dermatological conditions, diseases of the mucous of the oral and nasal cavities or diseases of the outer ear by administering a salt of hyaluronic acid (alkali, alkali metal, magnesium, aluminum or ammonium) combined with a pharmacologically active substance such as erythromycin. The hyaluronic acid fraction has an average molecular weight of 30,000 to 730,000 gm. The topical medicament can be applied as solids or in solution. The pharmaceutical composition is distinguishable for its reliance on only a hyaluronic acid salt and a multitude of pharmacological substances for ophthalmic use.

U.S. Pat. No. 4,006,224 issued on Feb. 1, 1977, to John F. Prudden describes a method and agent for treating inflammatory disorders of the gastrointestinal tract by administering 20 to 300 mg. per Kg. of body weight per day of D-glucosamine hydrochloride in either solid or liquid form. Lactose and cornstarch can be added for making tablets. The composition is distinguishable for its limitation to only D-glucosamine hydrochloride for treating gastrointestinal problems.

U.S. Pat. No. 5,252,339 issued on Oct. 12, 1993, to Manlio Cristofori et al. describes pharmaceutical compositions for oral intake containing glucosaminoglycan sulfate such as heparin, a thickening substance such as gum arabic, a plasticizer such as diethylphthalate, and a surfactant such as sodium cholate. The compositions make possible the absorption of the glycosaminoglycan sulfate in the intestine for performance of their anticoagulant, fibrinolytic, antithrombotic, antiatherosclerotic, and antihyperlipoproteinemic properties. The compositions are distinguishable for utilizing only one ingredient of the present invention.

U.S. Pat. No. 5,840,715 issued on Nov. 24, 1998, to Vito V. Florio describes a dietary regimen of a nutritional supplement composition containing gamma-linolenic acid, eicosapentaenoic acid and docosahexaneoic acid mixture, a mixture of chondroitin sulfate, N-acetyl glucosamine sulfate, glucosamine sulfate and manganese aspartate (Chondrox) for treating arthritis. The composition is distinguishable for requiring other organic acids with chondroitin sulfate and glucosamine sulfate.

French Patent Application NO. 2.035.781 published on Dec. 24, 1970, for Jean Dumazert describes a glucosamine-based medicament containing glucosamine chlorohydrate or acetyl glucosamine and a lipotropic agent such as either betaine, methionine or choline. The medicament is distinguishable for containing only glucosamine chlorohydrate or acetyl glucosamine and a lipotropic agent which are not included in the present invention.

German Patent Application No. DE 3445324 A1 published on Jun. 12, 1986, for Erich Enghofer et al. describes a synergistic composition for treatment of arthritis and contains glucosamine and an anti-exudative venous agent such as aescin or hydroxyethyl-rutoside. The composition is distinguishable for showing only glucosamine and requiring an anti-exudative venous agent.

U.K. Patent Application No. 896,940 published on May 26, 1962, for Chas. Pfizer & Co. describes a healing agent for wounds of the body surface containing glucosasmine and/or N-acetylglucosamine and glucosamine phosphate in a saline solution. The composition is distinguishable for requiring a phosphate salt of glucosamine.

Publications such as (1) Body Ammo Supplement, "Joint Connection Capsules", Product Alert, Oct. 27, 1997); (2) Arthred-G (Product Alert, Sep. 5, 1997); The Merck Index, 10th Edn., Entry No. 2297, 1983, pp. 2297 and 2298; (4) The Merck Index, 12th Edn., Entry No. 5747, 1996, p. 974; (5) Sigma Catalog, "Biochemicals, Organic Compounds for Research and Diagnostic Reagents"; and (6) H. Ansel et al., Ed., Pharma-ceutical Dosage Forms and Drug Delivery, Chapter 8, "Parenteral Medications and Sterile Fluids", 1995, pp. 286-336; describe, respectively, (1) a capsule for nutritional support of connective tissue comprising glucosamine sulfate, chondroitin sulfate and hyaluronic acid; (2) a powdered food supplement for reconstructing bone cartilage comprising glucosamine sulfate, chondroitin sulfate and hydrolyzed collagen; (3) citric acid as another alpha-hydroxy di-acid; (4) use of malic acid as a flavoring agent, flavor enhancer and acidulant in foods; (5) glucosamine compounds; and (6) shows injection information, electrolytes and vitamins.

These publications are distinguishable because only parts of the present inventive composition are shown. More than routine experimentation would be required to obtain the present invention.

Although many wound dressings exist, there is still a need for a wound dressing applicable in various forms, i.e., powder, gel, foam, paste or film, which will also reduce scars and repair connective tissues and a method of application, i.e., topically or injected, using the beneficial properties of hydrolyzed collagen as the basic ingredient for reduction of skin injuries such as bedsores, diabetic wounds, and the like without the addition of disinfectants such as alcohol and the like.

None of the above inventions and patents, taken either singularly or in combination, is seen to describe the instant invention as claimed. Thus, a composition and method for healing tissues solving the aforementioned problems is desired.

SUMMARY OF THE INVENTION

The present invention is a method and composition for healing tissues, promoting tissue and cell growth, protecting cells and tissues, and for the reduction of scar tissue and the repair of damaged animal tissues such as connective tissues by administering a medicinal composition comprising hydrolyzed collagen which serves as both the essential therapeutic ingredient and as a pharmaceutical carrier when combined with at least one other therapeutic agent. The medicinal composition containing hydrolyzed collagen as a carrier is preferably combined with hyaluronic acid or a salt thereof, or a polysulfated glycosaminoglycan, or a glucosamine salt, or mixtures thereof. The compositions of the present invention can be administered in any physical form such a powder, a gel, a paste, a foam, a film, a capsule, a tablet, a chewing gum, a topically applied patch with adhesive and with a reservoir system, a liquid which can be sprayed, taken orally or injected, and a rehydratable freeze-dried paste or sponge.

The compositions according to the present invention can be formulated as an oral or injectable nutritional preparation. In addition to hydrolyzed collagen, the oral and injectable nutritional preparations can include glucosamine hydrochloride, chondroitin sulfate, sodium hyaluronate, a manganese salt such as manganese ascorbate (U.S.P. food grade), and L-malic acid (U.S.P. food grade) which acts as a detoxifying agent by ridding the body of lactic acid often found in connective tissue.

It is believed that the underlying chemical mechanisms involved for the compositions of the present invention are as follows: (1) hydrolyzed collagen acts as a transport/carrier for the larger molecules of hyaluronic acid, chondroitin sulfate, glucosamine hydrochloride or sulfate; (2) hyaluronic acid is rapidly hydrolyzed upon contact with the treated tissue surfaces to the monosaccharides, i.e., glucuronic acid and N-acetyl glucosamine, and (3) chemical binding is enhanced chemotactically with the presence of hydrolyzed collagen.

The preferred main ingredient of the present compositions is hydrolyzed Type I collagen. The collagen is preferably derived from a bovine source such as any bovine bone or skin, and preferably from calves less than one year of age. The powder form has better hemostatic qualities than in a 60% gel form. The hydrogel, i.e., gel, can be made from 5% to 85%; active collagen. The collagen-containing composition is administered to the cleaned wound site where it absorbs the exudate, provides a physical barrier to bacterial infestation, reduces pain and expedites wound healing.

In another aspect, the composition may be formulated as a liquid eye drop in an aqueous solution prepared from hydrolyzed collagen in combination with compounds selected from hyaluronic acid or a hyaluronic acid salt, a polysulfated glycosaminoglycan or glucosamine salt, carboxymethylcellulose, a vasoconstrictor, such as tetrahydrozoline hydrochloride, and hypertonicity agents, such as sodium chloride and boric acid.

Accordingly, it is a principal object of the invention to provide a favorable environment that encourages wound healing and scar reduction.

It is another object of the invention to protect the wound bed and newly formed tissue including connective tissue.

It is a further object of the invention to conform to any wound site.

It is an object of the invention to control the evaporation of fluid, thereby acting as a barrier retaining a moist environment.

It is a further object of the invention to reduce pain at the wound site.

It is another object of the invention to protect the wound from bacterial infection.

It is a further object of the invention to increase chemotactic activity of the wound site.

Still another object of the invention is to enhance the body's natural healing ability by making resources readily available.

It is also an object of the invention to provide an oral or injectable nutritional composition for promoting the healing of wounds and tissues in humans and animals.

It is a further object of the invention to provide an injectable nutritional composition for tissue and cartilage repair of either a chronic or an acute nature.

Yet another object of the invention is to provide an oral or injectable nutritional composition for promoting the healing of wounds in animals containing hydrolyzed collagen, a glucosamine hydrochloride, sulfate, nitrate or iodide, chondroitin sulfate, sodium hyaluronate, and L-malic acid.

It is an object of the invention to provide improved elements and arrangements thereof for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The present compositions comprise hydrolyzed collagen, which not only serves as the main therapeutic component, but acts as a pharmaceutical carrier when preferably combined with a medicinal agent selected from the group consisting of hyaluronic acid and salts thereof, a polysulfated glycosaminoglycan, a glucosamine salt, and mixtures thereof to aid tissue and cells to grow and wounds to heal as quickly as possible.

In a preferred embodiment of the present invention, uncleaved hydrolyzed collagen is the main active ingredient. However, cleaved hydrolyzed collagen exhibits beneficial activity and can also be used. In uncleaved hydrolyzed collagen, the terminal peptide groups remain and are not lost or chemically altered in use. In cleaved collagen the terminal peptide groups are chemically removed during preparation or from the uncleaved product.

Hydrolyzed collagen has an increased number of chemically active sites as compared to native collagen. Native collagen typically has a molecular weight within the range of 100 to 300,000 Daltons. A native collagen molecule can have four chemically active sites. Therefore, not only is hydrolyzed collagen chemically more active, but its chemotactic properties are logarithmically increased versus that of native collagen. In addition, the hydrolyzed collagen composition of the present invention exhibits excellent thermal stability, which is not associated with native collagen.

Hydrolyzed collagen is defined as a collagen hydrolysate polypeptide having a molecular weight lower than native collagen, i.e., in the 100 to 300,000 Daltons range, and is derived by hydrolysis. Hydrolyzed collagen is commercially available in powdered form or an aqueous solution. Commercial preparation is typically accomplished by one of four methods: (1) alkaline hydrolysis; (2) enzymatic hydrolysis; (3) acid hydrolysis; and (4) synthetically by fermentation. Any of these methods can be used to derive the hydrolyzed collagen from either a bovine (bone and skin preferred), porcine, fish, avian or a synthetic source. The types of amino acid constituents and their sequences determine the beneficial healing qualities of hydrolyzed collagen. Hydroxylysine and hydroxyproline are amino acids found only in collagen and in no other medical protein hydrolysates. Hydroxylysine is typically found in concentrations from 0.7 to 1.2 wt. % in hydrolyzed collagen. Hydrolyzed collagen is well suited for use as a tissue adhesive, because it accelerates the healing process by functioning as a protective barrier and covering for forming tissues and cells.

The compositions of the present invention preferably contain hydrolyzed type I collagen as one ingredient having a molecular weight by definition ranging from 1,000 to 10,000 Daltons. This composition can contain a molecular weight from 50,000 to 100,000 Daltons of hydrolyzed collagen. The source of the collagen is preferably bovine and especially bovine bone or skin.

The tissue adhesive properties of hydrolyzed collagen allow for faster healing, and can, sometimes, negate the need for sutures or other closure means. The hydrolyzed collagen can be combined with hyaluronic acid, and/or glycosaminoglycans to further speed the healing process, decrease scarring and increase tissue strength.

Hyaluronic acid (HA) is rapidly hydrolyzed upon. contact with treated tissue surfaces to monosaccharides, glucuronic acid and N-acetyl glucosamine. Chemical binding is enhanced with the use of hydrolyzed collagen, i.e., it is chemotactic. Hyaluronic acid can be used via injection into a joint for its anti-inflammatory effect to relieve pain and suffering. This curative effect is inherently terminated when hyaluronic acid is consumed by the healing body.

Glycosaminoglycans (GAGs) are polysaccharides found in vertebrate and invertebrate animals. Several GAGs have been found in tissues and fluids of vertebrate animals. The known GAGs are chondroitin sulfate, keratin sulfate, dermatic sulfate, hyaluronic acid, heparin, and heparin sulfate. GAGs and collagen are the major structural elements of all animal tissue. Their synthesis is essential for proper repair, treatment, protection, and maintenance of all tissues.

Chondroitin sulfate, a polysulfated GAG, is a linear polymer occurring in several isomers, named for the location of the sulfate group. Chondroitin-4 sulfate is found in nasal and tracheal cartilages of bovines and porcines. It is also found in the bones, flesh, blood, skin, umbilical cord, and urine of these animals. Chondroitin-6 sulfate has been isolated from the skin, umbilical cord, and cardiac valves of the aforementioned animals. Chondroitin-6 sulfate has the same composition, but slightly different physical properties from the chondroitin-4 sulfate. These are the most common isomers used in the present invention. The polymers are also known as polysulfated glycosaminoglycans (PSGAGs), chondroitin polysulfate sodium, chondrin, sodium chondroitin polysulfate, and sodium chondroitin sulfate. For consistency, the term, "chondroitin sulfate", will be recited for all chondroitin sulfate isomers throughout this specification. Chondroitin sulfate is involved in the binding of collagen, and is also directly involved in the retention of moisture in the tissue. These are both valuable chemical properties that aid the healing process.

Hydrolyzed collagen in combination with GAGs, specifically a PSGAG such as chondroitin sulfate can be useful for the prevention and treatment of wound diseases. The hydrolyzed collagen combines with a PSGAG to bond or adhere selectively to tissue resulting in interference with and/or displacement of bacterial or other infectious agents. In addition, the combination product would exhibit anti-enzyme activity or the ability to inhibit enzyme activity.

The compositions of the present invention containing hydrolyzed collagen in combination HA and/or PSGAGs have been found to significantly reduce scarring at a wound site, because of enhanced wound healing rates. Thus, tissue strength of the healed wound site is greatly enhanced. The wound site closure rate and the lack of scar tissue are directly responsible for higher tissue strength in the closure area.

The hydrolyzed collagen accelerates the healing process by allowing an injured tissue to repair itself by producing and remodeling more collagen and other proteoglycans (PGs). The building blocks for collagen production are the amino acids found in hydrolyzed collagen. The hyaluronic acid and other proteoglycans (PGs) provide the framework for collagen production to follow. The PGs hold water to provide an excellent environment for healing of the tissue to begin. When in the wound site, any unused collagen that was produced is simply degraded to the amino acid. The rate-limiting step in the production of collagen is the conversion of glucose to glucosamine for the production of hyaluronic acid and other glycosaminoglycans (GAGs).

The medicinal compositions of the present invention can take the physical form used in topical administration selected from the group consisting of gel, spray, powder, paste, foam, film, and incorporation in a dressing bandage, a topically applied patch or in internal administration form selected from the group consisting of an injectable liquid and an orally ingestible liquid.

The powdered hydrolyzed collagen can be combined with either powdered hyaluronic acid or a 1% solution of hyaluronic acid sprayed secondarily to the primary dressing of hydrolyzed collagen. When both the hydrolyzed collagen and the hyaluronic acid are combined, the hydrolyzed collagen acts as carrier for the high molecular weight hyaluronic acid to the injured cell site. This combination forms an excellent environment by providing occlusion, i.e., to close off, and a moisturizing benefit.

The powder form will preferably have a moisture content of approximately 2-10 wt. % and a pH range of 5.5 to 6.5. The powder composition will have an ash content of less than 2.5 wt. % and an isotonic point of 5.0 to 6.5. In use, the powder composition may be the preferred physical form for use with irregularly shaped wounds. Tunnel wounds, flaps, and other non-conformative sites may be managed with the powder composition because it easily conforms to any shape wound, and may be applied by a poofer bottle or otherwise blown into difficult to reach wound sites. The powder is especially useful in wounds with a large amount of exudate, as the powder can absorb nearly 30 times its own weight. As the powder absorbs the exudate, a gel is formed which completely fills the wound site, forming a mechanical barrier against bacterial infection. The powder does not exhibit the characteristic fly-away when being applied to the wound site, and administration is perfected due to the precise powder placement.

The gel form of the medicament composition is especially useful in wounds with lesser amounts of exudate, burns, and surgical sites. Application of the gel can be dispensed through a tube, syringe or the reservoir in the topical patch. The gel is made of approximately 1-75 wt. % hydrolyzed Type I collagen and 1-99 vol. % water. It is preferable to use approximately 60 wt. % collagen. The gel is formed by adding sterile water to the powder. The gel has the added advantage of adding moisture to the wound site, inherent bacteriostatic properties and stays positioned where applied.

The present invention can be utilized in dental applications, wherein the gel form was utilized as a bacteriostatic agent for angular chelitis and resulted in exceptional tissue adhesion, accelerated wound healing, and tissue protection. The gel form can protect a high bacteria containing dental wound site such as the aforementioned angular chelitis, periodontal disease and other oral surgical sites. Therefore, by adding small amounts of chlorohexadine gluconate, parachloro-metaxylenol or other antimicrobial compounds, that the final product would be a "smart gel" capable of effective bacterial control and enhanced rates of healing wounds. It should be noted that utilizing antimicrobial compounds, per se, without the other ingredients would result in killing all the good and bad cells. It has been found that testing with various pain-killing materials such as benzocaine, that the hydrolyzed collagen as the major constituent in a base composition of glycerine, sorbitol and a cross-linking agent is an exceptional vehicle or carrier for incorporating other entities into the cell structure. They are effective wound healing agents when either used alone or with other entities such as antibacterials, microbials, zinc, alginate, aloe, vitamins C and E, native fibril collagen, and other proteoglycans and glycosaminoglycans. This product has been cleared by the Food and Drug Administration for the following dental indications: dental sore, oral ulcers, periodontal surgical wounds, suture sites, burns, extraction sites, and traumatic wounds which includes orthodontic bracket irritation, angular chelitis, and dry pockets.

A film form of the medicament composition may be made by mixing under heat at 155-175° F. the powdered form with deionized water. Cross-linking and other agents such as humectant, propylene glycol, sorbitol, and glycerine are added to the mixture. A preservative such as benzyl alcohol or paraben can be added. The mixture is cast on a belt liner by knife on a roll coating machine to form a liquid film which is oven-dried. The film form can also be formed by a cooling the liquid solution. These films can be used for drug or other chemical delivery, and especially in dental applications. Antimicrobial and other medicinal agents can also be added to the film as needed for specific applications.

It is known that hyaluronic acid can be injected into an injured joint for its anti-inflammatory effect. Further benefits are the relief of pain and swelling. These effects disappear when the hyaluronic acid is consumed by the injured body portion. The hyaluronic acid is believed to accelerate the initiation of the healing process by allowing the injured tissues to repair by manufacturing and remodeling more collagen and other proteoglycans. The building blocks for collagen production are the amino acids found in the hydrolyzed collagen. The hyaluronic acid and other proteoglycans provide the framework for collagen production to follow. The proteoglycans hold water to provide for an excellent environment for the healing process to begin. Any unused collagen that was produced is simply degraded back to the amino acids. The proteoglycans have an inherent rate-limiting production. The rate limiting step is the conversion of glucose to glucosamine for the production of hyaluronic acid and other glycosaminoglycans.

The hydrolyzed collagen acting as a carrier of hyaluronic acid which enhances the absorption of large molecules, provides for healing effects and an environment conducive to healing. The present invention provides for the body's ability to continue to convert the hydrolyzed collagen into proteoglycans for aiding the repair of both connective tissue and other tissues in humans and animals.

In another embodiment of the present invention, hydrolyzed collagen and hyaluronic acid are further combined with polysulfated glycosaminoglycans, glucosamine hydrochloride or sulfate to provide an oral or injectable nutritional composition for repair of wounds and tissue. Glycosaminoglycans and collagen are the chief structural elements of all tissues. Their synthesis is essential for proper repair, treatment, protection, and maintenance of all tissues. The oral and injectable nutritional compositions of present invention preferably include in addition to hydrolyzed collagen, glucosamine hydrochloride, chondroitin sulfate, sodium hyaluronate, a manganese salt, and L-malic acid (U.S.P. food grade). A major advantage of the present invention is the perfecting of a vehicle which allows for the formulations of excellent preparations free from concentration gradients of the active substances, and which, therefore, are perfectly adhesive, somewhat transparent and homogeneous without potential sensitization effects. The inventive compositions can include salts such as sodium, potassium, calcium, barium, magnesium, aluminum, and the like and various antimicrobials and antibiotics. Therefore, these salts can be added to produce gels, ointments, creams, and inserts.

The hydrolyzed collagen can be used as an excellent drug vehicle system containing acidic, neutral or complexed drug medications.

Testing of a composition of hydrolyzed collagen and a 1% solution of hyaluronic acid was performed on full thickness wounds in mice. The applied composition on wounds and scars resulted in reduced scar formation and faster healing rates. In combination with a polysulfated glycosaminoglycans alone and with 1% hyaluronic acid, exceptional tissue granulation was observed. With the use of the polysulfated glycosaminoglycans, a novel method of dressing a wound site was used by injecting the composition directly into and under the thin film wound dressing without ever exposing the wound site to further environmental contamination. The hydrolyzed collagen can be used for the first few days of treatment, followed by the injection of the polysulfated glycosaminoglycans to the wound closure. Thus, hydrolyzed collagen was shown to be an efficient vehicle capable of enhancing the bioavailability of hydrolyzed collagen and other glycosaminoglycans, and strengthening their activity.

In other applications, hydrolyzed collagen in combination with hyaluronic acid and polysulfated glycosaminoglycans can be used as a protective agent prior to and after surgery to minimize cell damage and to expedite wound healing. This combination can be used during surgery to foster separation of tissue to prevent adhesion formation. It is noted that when hydrolyzed collagen is used alone, it becomes an excellent tissue adhesive, but when combined with other proteoglycans, it assumes a chemotactic position for use in accelerated wound healing.

The delivery systems for providing the inventive composition to a wound are manifold. In powder form, various delivery systems are packets, bottles, unit dosages, and aerosols. In paste form, the hydrolyzed collagen in water composition is delivered in either jars, open containers, tubes, reservoir island dressings or filmed reservoirs. In spray form, the hydrolyzed collagen composition is delivered in liposome carriers with a pump container containing aerosol or in water. A liposome carrier is defined as an artificial vesicle composed of one or more concentric phospholipid bilayers. In foam form, conventional foams are impregnated with either the gel or powder form of the hydrolyzed collagen compositions. In sponge or paste form, the composition can be supplied as a rehydratable freeze-dried form. In injectable form, the hydrolyzed collagen compositions are water-based.

It has been found that the compositions containing hydrolyzed collagen combined with hyaluronic acid and/or glycosaminoglycans act as tissue cell protectorants. Therefore, these compositions can also be used for preserving tissue or organ implants such as donor organs. A preservative composition in solution form can comprise 5% hydrolyzed collagen, 3% of a 1% solution of hyaluronic acid, and 3% polysulfated glycosaminoglycans in wt./wt. in water.

It has been also found that compositions of a hydrolyzed collagen and/or polysulfated glycosaminoglycans can be utilized in film form to avoid undesired adhesions between injured surfaces. An added advantage that the film form is biodegradable and can be utilized by natural means in in vivo degradation in the living body.

In the situation of diabetic patients with open sores and wounds, oral treatment with compositions containing hydrolyzed collagen, glucosamine hydrochloride or sulfate, chondroitin sulfate, and L-malic acid has been found to be very effective. In addition, vitamins A, C and E with magnesium oxide, chelated manganese, grape seed extract, zinc, chromium picolinate, selenium, and glycosaminoglycans can be added to produce a nutrient composition for oral intake.

It has been established that the hydrolyzed collagen used as a carrier in powder form, paste or a lyophilized foam has hemostatic qualities when combined with thrombin to improve healing of wounds. Antimicrobials can be combined with the hydrolyzed collagen to further enhance its bacteriostatic quality, as can antibiotics, such as tetracycline, streptomycin, cephalosporin and antibacterials, such as iodine, parachlorometaxylenol, and chlorhexidine gluconate or acetate.

Hydrolyzed collagen combined with a polysulfated glycosaminoglycans such as chondroitin sulfate will also prevent wound diseases. The hydrolyzed collagen combines with a polysulfated glycosaminoglycans to bond or adhere selectively to tissue resulting in interference with and/or displacement of bacterial or other infectious agents. In addition, the combination product would inhibit anti-enzyme activity.

It has been found that the following composition has provided the above-mentioned beneficial results in both animals and humans. The unit dose will be described for a human in terms of dosage per bodyweight. Animals may require larger doses due to larger weights.

(1) Glucosamine hydrochloride or other salts of glucosamine such as the sulfate, nitrate or iodide, which are obtained from either synthetic, bovine or porcine sources having a molecular weight range from 5,000 to 30,000 Daltons.

(2) Chondroitin sulfate, Type A (chondroitin-4-sulfate). Type B (chondroitin-5-sulfate), and/or Type C (chondroitin-6-sulfate, obtained through fermentation or extraction of bovine trachea, other bovine or porcine sources. A molecular weight range of 5,000-50,000 Daltons can be used, with a preferred range of 25,000-35,000 Daltons.

(3) Hydrolyzed Type I collagen, preferably natural hydrolyzed collagen powder having a pH of 5.0-6.5, and obtained from the bone, skin and tissue of a bovine calf less than a year old. Preferably, the hydrolyzed Type I collagen has a molecular weight range no greater than about 1,000 to about 1,500 Daltons.

(4) Sodium hyaluronate obtained from either synthetic, bovine or avian sources with a molecular weight range from about 50,000 to about 3,500,000 Daltons.

(5) Manganese ascorbate, U.S.P. food grade.

(6) L-malic acid, U.S.P. food grade, acts as a detoxifying agent by ridding the body of lactic acid often found in connective tissue.

For injectable use, the above substances will be dissolved in sterilized water and buffered with citric acid or sodium chloride to improve shelf life. The pH can be adjusted with conventional agents. Also, preservatives such as ethylenediaminetetraacetic acid (EDTA), benzyl alcohol, and benzalkonium chloride can be added. Powdered, encapsulated or pilled compositions to be taken orally by either humans or animals are base on mg/kg bodyweight and described in the following order of (a) a preferred concentration, (b) an optional range, and (c) a broad range in terms of the aforementioned numbered ingredients (1) to (6).

(1): (a) 5 mg.; (b) 3-8 mg.; (c) 2-10 mg.
(2): (a) 3.5 mg.; (b) 1-6 mg.; (c) 1-8 mg.
(3): (a) 4 mg.; (b) 3-15 mg.; (c) 2-20 mg.
(4): (a) 5 mg.; (b) 2-6 mg.; (c) 1-7 mg.
(5): (a) 1 mg.; (b) 0.5 mg.; (c) 0.5-3 mg.
(6): (a) 5 mg.; (b) 0.2 mg.; (c) 0.2-6 mg.

For injectable use in humans, the following compositions are recommended as a first preference, a second preference and a third preference. First: (1), (2), (4); second: (1) to (4); and third: (1) to (6).

For injectable use in animals, the following compositions are recommended as first, second and third preferences. First: (1), (2), (4); second: (1), (2), (4), (6); third: (2) to (6); fourth: (1) to (4); and fifth: (1) to (6).

In terms of injectable solutions in weight of ingredient per volume of a sterilized aqueous solution for human and animal, the following preferred concentrations and ranges are: (1) 150 mg./ml., 10-1,000 mg./ml.; (2) 150 mg./ml., 5-1,500 mg./ml.; (3) 2-100 mg./ml.; and (4) 5 mg./ml., 1-30 mg./ml. However, ingredients (5) and (6) can be added, i.e., manganese ascorbate and L-malic acid.

Unlike the compositions described in the prior art, it is believed that the present composition provides an enhanced chondroprotective effect by providing foundational support for the creation of new body tissue and cartilage growth in mammals because it comprises hydrolyzed Type I collagen having a preferred molecular weight average no greater than 2,000 Daltons. More preferably, the hydrolyzed Type I collagen has a molecular weight average of about 1,000 to 1,500 Daltons. It is believed that the hydrolyzed Type I collagen having a preferred weight average no greater than about 2,000 Daltons, acts as a transporter or carrier for the larger molecules of sodium hyaluronate and/or chondroitin sulfate by aiding in the absorption process of these large molecules, thereby increasing the bio-availability of each.

The following case studies illustrate the benefits of hydrolyzed collagen applied to various tissue damage situations.

Case study 1: A diabetic patient had an advanced wound of a 14 year old graft site 5.4 by 1.8 cm. in area from amputation of 15% of one infected foot. The patient received weekly applications of biodegradable hydrolyzed collagen in powder and gel form absent preservatives or alcohols. The wound healed in 27 days.

Case study 2: A patient having pressure ulcers or bedsores and post-surgical wounds from first and second degree burns. A gel and powder barrier of hydrolyzed collagen and debridement therapy for two days removed the eschar and minimized scarring.

Case study 3: An open wound was treated with Type I collagen hydrolysate containing 19 amino acids with the powder and gel forms which were never removed. The powder form was blown into the cavity and the gel form was topically added. When Type I collagen, being stronger, was added to infants and small children having wounds, scarring was minimal and superficial cuts and burns healed rapidly.

Case study 4: A foot wound of a diabetic patient showed signs of infection, reddened, painful, foul smell of the drainage, gangrene, and a large ulcer. The wound was washed with saline solution, collagen hydrolysate powder was added topically. Saran wrap covered the wound and was secured by tape. The dressing was changed daily for a successful cure.

Case study 5: An ankle ulcer of a diabetic patient showed dysfunction (loss of feeling), and a yellowish exudate which was cleaned with a saline solution. Debridement was performed with a soft brush wet with saline solution. Hydrolyzed collagen powder was applied and non-stick pad was secured with adhesive tape. The dressing was changed daily for a successful recovery.

Case study 6: For an advanced wound, Type I hydrolyzed collagen in the gel form was applied and noticeably reduced scarring and blocked nerve pain.

Case study 7: A female patient had 1,000 sutures resulting from an liposuction operation. Application of hydrolyzed collagen was added in gel form and the wounds healed in six days.

Case study 8: A 54 year old paraplegic male patient having a Stage 3 pressure ulcer on the heel of his deformed atrophic foot was treated with hydrolyzed collagen and cured in 5 weeks.

Case study 9: A 69 year old male patient having a history of venous stasis ulcers and a bacterial infection on dorsum of foot was previously treated with calcium alginate for over a year. Hydrolyzed collagen was administered with antibiotics and the wound was completely healed in 3 months.

Case study 10: A 46 year old female patient developed an infection in her jaw in the area of her enioglossus pull through. Hydrolyzed collagen was applied twice a day until she was cured in one month.

Case study 11: Three patients having at least a two year history of pilonidal cysts on their buttocks were treated with a bacteriostatic hydrogel sheet and hydrolyzed collagen powder to be cured in 3 to 6 months.

Case study 12: A 77 year old patient had a penetrating gastric ulcer and periesophageal hernia which required surgical repair. After 10 days, the patient had a surgical abscess which was treated with calcium alginate for a month without any wound healing. Then hydrolyzed collagen powder treatment was initiated with wound closure in 30 days, and a full recovery in 36 days.

Case study 13: A 5.4 cm. by 1.8 cm. wound on a 14 year old graft site on a lower left leg of a patient was initially treated with an enzymatic debrider and a hydrocolloid cover. Calcium alginate was added a week later, but there was minimal closure. Hydrolyzed collagen was applied and covered with calcium alginate and a hydrocolloid. In three months, there was wound closure.

Case study 14: A 30 year old male patient suffering from a deep chronic ulcer on the right medial malleolus due to a vehicular accident was treated with hydrolyzed collagen daily and the 3 cm. long, 0.8 cm. wide and 0.5 cm. deep wound healed in 7 months.

Case study 15: A female at-home patient having a pressure wound on one heel was treated antibiotics but resisted wound healing for a month. Hydrolyzed collagen was administered for 3.5 months with a complete recovery and wound closure.

Case study 16: A 56 year old overweight female patient had a traumatic left heel injury with resulting surgical repair of the Achilles tendon. The wound measured 2.0 cm.×0.8 cm.×0.1 cm. with a yellow slough and considered a Stage III wound. For almost two months, other medications were utilized without any improvement. Then hydrolyzed collagen gel treatment was initiated when the wound measured 4.2 cm.×0.7 cm. with peri-wound redness and edema. The gel treatment provided wound healing and decreased the wound size within the first week of treatment and no sign of infection throughout the treatment.

Case study 17: The hydrolyzed collagen gel composition was found superior to other hydrogels. The honey-like consistency of the invention was advantageous in keeping the medication where it is applied and did not add to the exudate load, especially in the tunneling wound. This feature makes it more feasible to apply transparent film dressings over the gel rather than a gauze or even a non-stick pad, thus increasing the visibility of the wound bed between dressing changes.

Case study 18: The gel form of hydrolyzed collagen was used on a degloving injury on a small dog with very good results.

Case study 19: The gel form of hydrolyzed collagen was used on a cat having a chronic corneal ulcer for at least two months, which would have needed enucleation of the eye. The eye healed in less than three weeks and did not leave a noticeable scar.

Case study 20: A dog's elbow with a chronic skin ulcer healed in three weeks by adding the hydrolyzed collagen composition. Foot pad lacerations with or without a bandage also healed dramatically within two weeks.

Case study 21: A dog's foot pad lacerations also healed dramatically within two weeks with treatment of the hydrolyzed collagen composition.

Case study 22: A dog suffered from an inguinal wound 5 cm. by 1 cm. which extended through the fascia to the muscle sheath and became infected. Hydrolyzed collagen powder was added topically to the wound and interacted with the wound exudate to form a gel which dried to a protective coating. By the fourth day of treatment, the wound was covered with a newly formed granulation tissue bed. On the tenth day, a healthy bed of granulation tissue had formed. On the fifteen day, skin contraction was evident, and the wound was left uncovered to heal without a bandage. On the twenty-first day, the wound was completely healed.

Case study 23: A stray poodle was found with an injury of the lateral aspect of the left tarsus, starting at the hock and extending distally. The wound measured 8 cm. by 3 cm. and covered 25-50% of the circumference of the leg. The wound was treated for three days with hydrolyzed collagen powder, wherein a gel with the exudate was formed which provided a moist healing environment conducive to healing. A newly formed granulation tissue bed had formed. After the sixth day after application every 2 to 3 days, a betadine soak was used to debride necrotic tissue. The wound site was reduced to 5.5 cm. by 1.2 cm. at the hock. After 16 days of treatment, there was increased skin contracture and good epithelialization of the wound bed, with the wound measuring 5 cm. by 0.4 cm. at the tarsus and at the hock. Three days later, the wound was left to heal without a bandage. In three weeks and four days, the wound had healed completely.

In these case studies, neither preservatives nor alcohols were used.

In yet another embodiment the composition containing hydrolyzed collagen can be formulated as a liquid eye drop. The liquid eye drop formulation of the present invention is an aqueous solution prepared from hydrolyzed collagen in combination with compounds selected from hyaluronic acid or a hyaluronic acid salt, a polysulfated glycosaminoglycan or glucosamine salt, carboxymethylcellulose, tetrahydrozoline hydrochloride, and hypertonicity agents, such as sodium chloride and boric acid.

Hydrolyzed collagen serves as a pharmaceutical carrier for active and inactive ingredients in the solution. The collagen may be derived from any source, including porcine sources, fish, chicken (poultry), bovine sources, and synthetic/fermentation procedures. Hydrolyzed collagen functions to provide healing and lubricity to the eye tissue and surrounding membrane, as well as providing a soothing and calming effect on the eye. It is highly chemotactic in that it attracts other chemical compounds selectively to aid in the healing process.

Hyaluronic acid, often provided as the sodium salt, sodium hyaluronate, has been used in previous work with the eye, but in such applications hyaluronic acid has not been used in conjunction with hydrolyzed collagen and other actives, such as carboxymethylcellulose, tetrahydrozoline hydrochloride, and polysulfated glycosaminoglycans. Hyaluronic acid is native to the eye and is an anti-inflammatory. Hyaluronic acid provides lubricity to the eye tissues thus healing and comforting the eye tissues. Hyaluronic acid may be used as a carrier to provide an environment in the eye for tissue repair.

In the present composition, the polysulfated glycosaminoglycan primarily provides tissue healing, but also is an anti-inflammatory, acts as a lubricant, and serves as a carrier for other active ingredients. Polysulfated glycosaminoglycan is native to the body and has synergistic effects when combined with hyaluronic acid and hydrolyzed collagen. The type of polysulfated glycosaminoglycan used in the composition are isomers of chondroitin sulfate, such as chondroitin sulfate A, B and C.

The composition may contain carboxymethylcellulose, which provides lubricity and is a demulcent. The composition may also contain a vasoconstrictor, such as tetrahydrozoline HCl, ephedrine HCl, or naphazoline HCl, and hypertonicity agents, such as sodium chloride and boric acid.

Preservatives such as benzalkonium chloride and edetate disodium may be used in the composition. Adjustments to the pH are made by using hydrochloric acid and sodium bicarbonate, as needed. The pH is adjusted to a range between 7.1 to 7.3.

The ranges of the active ingredients in the aqueous eye drop composition are as follows:

|  | Range (% wt.) |
| --- | --- |
| Hyaluronic acid | 0.01-25 |
| Hydrolyzed collagen | 0.01-15 |
| Polysulfated glycosaminoglycan | 0.01-20 |
| Carboxymethylcellulose | up to 5.0 |
| Tetrahydrozoline hydrochloride | up to 5.0 |
| Sodium chloride/Boric acid | up to 8.0 |

Variations of the composition may be had utilizing hydrolyzed collagen as a common ingredient. The composition may include:
sodium hyaluronate
hydrolyzed collagen
Chondroitin sulfate/PSGAG
CMC
Tetrahydrozoline HCL
Sodium chloride
Boric acid
Hydrochloric acid (pH 7.1-7.3)
Sodium bicarbonate (pH 7.1-7.3)
Purified water
Benzalkonium chloride
Edetate disodium The aforementioned twelve ingredients may be combined in any variation, the following being formula examples denoted in % wt. by wt. In a first variation, the composition includes:

| | |
|---|---|
| Sodium hyaluronate | 0% |
| Hydrolyzed collagen | 0.01% |
| Chondroitin sulfate/PSGAG | 0% |
| CMC | 2.5% |
| Tetrahydrozoline HCl | 0.05% |
| Sodium chloride | 1.0% |
| Boric acid | 1.0% |
| Hydrochloric acid | As needed |
| Sodium bicarbonate | As needed |
| Purified water | As needed |
| Benzalkonium chloride | 0.01% |
| Edetate disodium | 0.5% |

In a second variation, the composition includes:

| | |
|---|---|
| Sodium hyaluronate | 0.5% |
| Hydrolyzed collagen | 0.1% |
| Chondroitin sulfate/PSGAG | 0.5% |
| CMC | 1.0% |
| Tetrahydrozoline HCl | 0.05% |
| Sodium chloride | 1.0% |
| Boric acid | 1.0% |
| Hydrochloric acid | As needed |
| Sodium bicarbonate | As needed |
| Purified water | As needed |
| Benzalkonium chloride | 0.01% |
| Edetate disodium | 0.5% |

In a third variation, the composition includes:

| | |
|---|---|
| Sodium hyaluronate | 1.0% |
| Hydrolyzed collagen | 0.5% |
| Chondroitin sulfate/PSGAG | 1.0% |
| CMC | 0% |
| Tetrahydrozoline HCL | 0% |
| Sodium chloride | 1.0% |
| Boric acid | 1.0%% |
| Hydrochloric acid | As needed |
| Sodium bicarbonate | As needed |
| Purified water | As needed |
| Benzalkonium chloride | 0.01% |
| Edetate disodium | 0.5% |

In a fourth variation, the composition includes:

| | |
|---|---|
| Sodium hyaluronate | 5.0% |
| Hydrolyzed collagen | 3.0% |
| Chondroitin sulfate/PSGAG | 5.0% |
| CMC | 0.01% |
| Tetrahydrozoline HCL | 0.01% |
| Sodium chloride | 1.0% |
| Boric acid | 1.0% |
| Hydrochloric acid | As needed |
| Sodium bicarbonate | As needed |
| Purified water | As needed |
| Benzalkonium chloride | 0.01% |
| Edetate disodium | 0.5% |

It is to be understood that the present invention is not limited to the embodiments described above, but encompasses any and all embodiments within the scope of the following claims.

We claim:

1. A method for achieving an effect in a patient comprising administering a therapeutically effective amount of a medicinal composition to the patient, wherein the effect is for treating eye tissue and ulcers, for removing redness of the eye, for providing lubrication for the eye, for providing moisture for eye dryness, for relieving eye pain, for promoting tissue and cell growth, for protecting cells and tissues, for reducing scar tissue and repairing damaged animal tissues, or for topical wound care, wherein the composition comprises hydrolyzed Type I collagen having an average molecular weight ranging from 1,000 to 10,000 Daltons and 0.01-15% wt. of the medicinal composition, at least one therapeutic agent selected from the group consisting of hyaluronic acid and salts thereof, a polysulfated glycosaminoglycan, carboxymethylcellulose, and tetrahydrozoline hydrochloride, the hydrolyzed collagen serving as a pharmaceutical carrier for said at least one therapeutic agent.

2. The method according to claim 1, wherein said composition further comprises a hypertonicity agent selected from the group consisting of sodium chloride and boric acid, the hydrolyzed collagen serving as a pharmaceutical carrier for said at least one hypertonicity agent.

3. The method according to claim 2, wherein said composition further further includes a preservative.

4. The method according to claim 3, wherein said preservative comprises benzalkonium chloride.

5. The method according to claim 3, wherein said preservative comprises edetate disodium.

6. The method according to claim 1, wherein said composition comprises a form selected from the group consisting of a powder, a gel, a foam, a paste, and a film.

7. The method according to claim 1, wherein said composition comprises an aqueous solution and a pH between 7.1 and 7.3.

* * * * *